United States Patent
He et al.

(10) Patent No.: US 6,423,057 B1
(45) Date of Patent: Jul. 23, 2002

(54) METHOD AND APPARATUS FOR MONITORING AND CONTROLLING TISSUE TEMPERATURE AND LESION FORMATION IN RADIO-FREQUENCY ABLATION PROCEDURES

(75) Inventors: Ding Sheng He; Michael Bosnos; Frank Marcus, all of Tucson, AZ (US)

(73) Assignee: The Arizona Board of Regents on behalf of The University of Arizona, Tucson, AZ (US)

( * ) Notice: Subject to any disclaimer, the term of this patent is extended or adjusted under 35 U.S.C. 154(b) by 0 days.

(21) Appl. No.: 09/488,878

(22) Filed: Jan. 21, 2000

Related U.S. Application Data

(60) Provisional application No. 60/117,088, filed on Jan. 25, 1999, and provisional application No. 60/137,589, filed on Jun. 4, 1999.

(51) Int. Cl.[7] ............................................... A61B 18/04
(52) U.S. Cl. .............................. 606/34; 606/45; 606/49
(58) Field of Search .............................. 606/34, 37–43, 606/45, 48–50; 607/100, 101, 99, 105, 98, 102

(56) References Cited

U.S. PATENT DOCUMENTS

| | | | | |
|---|---|---|---|---|
| 4,140,109 A | * | 2/1979 | Savic et al. | |
| 6,066,139 A | * | 5/2000 | Ryan et al. | 606/50 |
| 6,112,123 A | * | 8/2000 | Kelleher et al. | 607/98 |
| 6,123,702 A | * | 9/2000 | Swanson et al. | 606/34 |
| 6,217,574 B1 | * | 4/2001 | Webster | 606/41 |

* cited by examiner

*Primary Examiner*—Roy D. Gibson
(74) *Attorney, Agent, or Firm*—Antonio R. Durando

(57) ABSTRACT

Impedance and capacitance-related parameters are monitored in the electrical circuit of a tissue-ablation apparatus wherein RF electrical power is administered at predetermined frequencies. Tissue temperature has been found to correlate well with low-frequency impedance, or with the resistive component of impedance at any frequency. Therefore, one or both of these parameters are calculated and tracked during the ablation procedure to estimate tissue temperature. Similarly, tissue lesion formation has been found to correlate well with changes in the capacitive component of tissue impedance. Thus, this parameter can be used to track tissue lesion formation during the ablation procedure. The ratio of tissue-to-blood interface with the ablation electrode is estimated by measuring impedance at a very low frequency and a very high frequency. The difference between these two values divided by the high-frequency value is taken to be a measure of such ratio. Alternatively, other electrical parameters indicative of changes in the capacitive component of the system may be measured and the ratio is calculated as a function of these changes with respect to a baseline value.

22 Claims, 10 Drawing Sheets

METHOD AND APPARATUS FOR MONITORING AND CONTROLLING TISSUE TEMPERATURE AND LESION FORMATION IN RADIO-FREQUENCY ABLATION PROCEDURES

RELATED APPLICATIONS

This application is based on Provisional Application No. 60/117,088, filed on Jan. 25, 1999, and on Provisional Application No. 60/137,589, filed on Jun. 4, 1999.

BACKGROUND OF THE INVENTION

1. Field of Invention

This invention relates generally to tissue ablation and, in particular, to a lesion monitoring technique for controlling the removal of cardiac tissue to correct arrhythmias.

2. Description of the Related Art

Currently there are several medical and surgical treatments for abnormal rapid heart rhythms (arrhythmias). Medical treatments are usually attempted first with anti-arrhythmic drugs that control the arrhythmia by slowing cardiac conduction. When these treatments fail, surgical interventions become necessary.

One such form of intervention is cardiac ablation, a procedure that involves the removal of ventricular or atrial tissue to eliminate abnormal rapid heart rhythms by affecting cardiac conduction. Radio-frequency (RF) catheter ablation is a technique in which radiofrequency energy is delivered, via catheter, to a metallic electrode placed in contact with tissue within the heart. This energy causes tissue heating, which in turn produces the formation of a lesion. Radiofrequency catheter ablation has become a principal form of therapy for paroxysmal supraventricular tachycardia (rapid heart rhythm originating in the atria) and is also being used in an increasing number of patients for treatment of ventricular tachycardia (abnormal rapid rhythm originating in the ventricles) associated with coronary artery disease and other forms of heart disease. Ventricular tachycardia is a type of arrhythmia with high morbidity and mortality. RF current delivered through a standard 7F or 8F, 4 or 8 mm distal electrode has been highly successful for ablation of arrhythmogenic tissue that is critical to the initiation and maintenance of the arrhythmia. That is accomplished by placing the ablation electrode against the tissue, such as through accessory atrioventricular pathways (in patients with Wolff-Parkinson-White syndrome) and the atrial end of the slow atrioventricular-nodal pathway (in patients with atrioventricular nodal reentrant tachycardia). However, in approximately 1 to 10 percent of patients with accessory pathway and in 30 to 50 percent of patients with ventricular tachycardia associated with a healed myocardial infraction, the arrhythmogenic tissue may be located at the epicardial border zone and the RF energy delivered to the endocardium may not be sufficient to eliminate the arrhythmogenic tissue. In such cases, deeper lesions are necessary for a successful ablation procedure and adequate control of lesion formation becomes critical to avoid excessive tissue damage.

Under current practice, the catheter is guided through a vessel under fluoroscopy or equivalent technique to an appropriate site in the patient's heart, where the electrode is positioned in the blood stream against the tissue to be ablated. It is important that contact between the electrode and the tissue be maximized in order to direct the RF energy toward the formation of tissue lesion rather than through the ambient blood phase. It is known that the impedance of the electrical system increases with greater contact of the electrode with the heart tissue. Therefore, this fact is used to ascertain when sufficient contact is established between the electrode and the heart tissue for carrying out the ablation procedure. A baseline impedance is measured when the electrode is known to reside entirely within the blood stream, and contact with tissue is assumed to have occurred when the impedance has increased by a predetermined amount set empirically for a given system.

It has been shown that tissue temperature must exceed 45–50° C. for lethal tissue damage and lesion formation to occur, but the temperature cannot be so high (i.e., about 100° C.) as to produce carbonization of the tissue and/or coagulation of the blood. For any given electrode size and tissue contact area, the RF-induced lesion size is a function of the RF power level and exposure time. Therefore, the objective of the procedure is to administer enough energy to heat the tissue to a temperature sufficiently high to induce a lesion and to achieve the desired degree of lesion formation, without also causing tissue carbonization or blood coagulation. Presently, the ablation procedure is carried out entirely on the basis of experience and empirical data. When the surgeon is satisfied that sufficient electrode/tissue contact exists based on a measurement of impedance, a certain amount of energy is delivered at a frequency within the RF range, typically at 250–500 kHz. The power input is maintained for a period of time known to be safe and reasonably effective to produce a useful depth of lesion. In some cases, a temperature sensor is coupled to the electrode in the catheter, so that the ambient temperature can be monitored to avoid an excessive rise and provide a useful parameter for monitoring progress during the procedure. Some systems include a feedback control system that adjusts RF power input to maintain the temperature constant after it has reached a predetermined set level considered optimal for ablation.

The problems with this prior-art methodology are that it relies almost entirely on educated guess work based on experience and past empirical data. If a temperature sensor is available, it provides a measure of the bulk temperature of the system, specifically at the location where the sensor lies, but it does not measure precisely the temperature of the tissue being treated, which is necessarily somewhat removed from the sensor's location. Thus, excessive heating may be produced in the tissue even though it is not observed through the sensor. Another problem lies in the lack of ability to measure the depth of the lesion being produced during ablation. The power level and duration of RF energy delivery is set to produce a desired result based on experience, but the depth of the lesion actually produced cannot be monitored or controlled.

Therefore, there is a need for an ablation technique that includes a more precise indication of the temperature and depth of lesion of the tissue being treated. The present invention provides qualitative and quantitative measures of these parameters during the ablation procedure based on impedance measurements and on measurements of electrical parameters indicative of a change in the capacitance of the tissue.

BRIEF SUMMARY OF THE INVENTION

The main objective of the invention is to provide a surgeon with an indication of the depth or volume of the tissue lesion produced by the administration of RF energy during the course of an ablation procedure, so that a progress can be monitored during the procedure and lesion formation can be optimized.

Another important objective is also to provide a measure of the temperature of the tissue being treated, so that the physician may benefit from current information regarding the onset of ablation and the potential for tissue carbonization and/or blood coagulation resulting from an excessive temperature rise as the procedure progresses.

Another important goal is a technique for estimating the tissue-to-blood ratio of interface with the ablation electrode, so that the physician may place the electrode in an optimal position against cardiac tissue.

Another goal of the invention is an approach that is suitable for implementing automatic control schemes based on electrical measurements that correlate quantitatively to tissue temperature and depth of lesion.

Still another goal of the invention is a method and apparatus that are suitable for implementation with existing instruments.

A final object is a procedure that can be implemented easily and economically according to the above stated criteria.

In accordance with these and other objectives, the invention consists of monitoring impedance and capacitance-related parameters in the electrical circuit of a tissue-ablation apparatus wherein RF electrical power is administered at predetermined frequencies. Tissue temperature has been found to correlate well with low-frequency impedance, or with the resistive component of impedance at any frequency. Therefore, one or both of these parameters are calculated and tracked during the ablation procedure to estimate tissue temperature. Similarly, tissue lesion formation has been found to correlate well with changes in the capacitive component of tissue impedance. Thus, this parameter can be used to track tissue lesion formation during the ablation procedure.

The invention further teaches to estimate the ratio of tissue-to-blood interface with the ablation electrode by measuring impedance at a very low frequency and a very high frequency. The difference between these two values divided by the low-frequency value is taken to be a measure of such ratio. Alternatively, other electrical parameters indicative of changes in the capacitive component of the system may be measured and the ratio is calculated as a function of these changes with respect to a baseline value.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiments and particularly pointed out in the claims. However, such drawings and description disclose only some of the various ways in which the invention may be practiced.

DETAILED DESCRIPTION OF THE INVENTION

Figure 1:
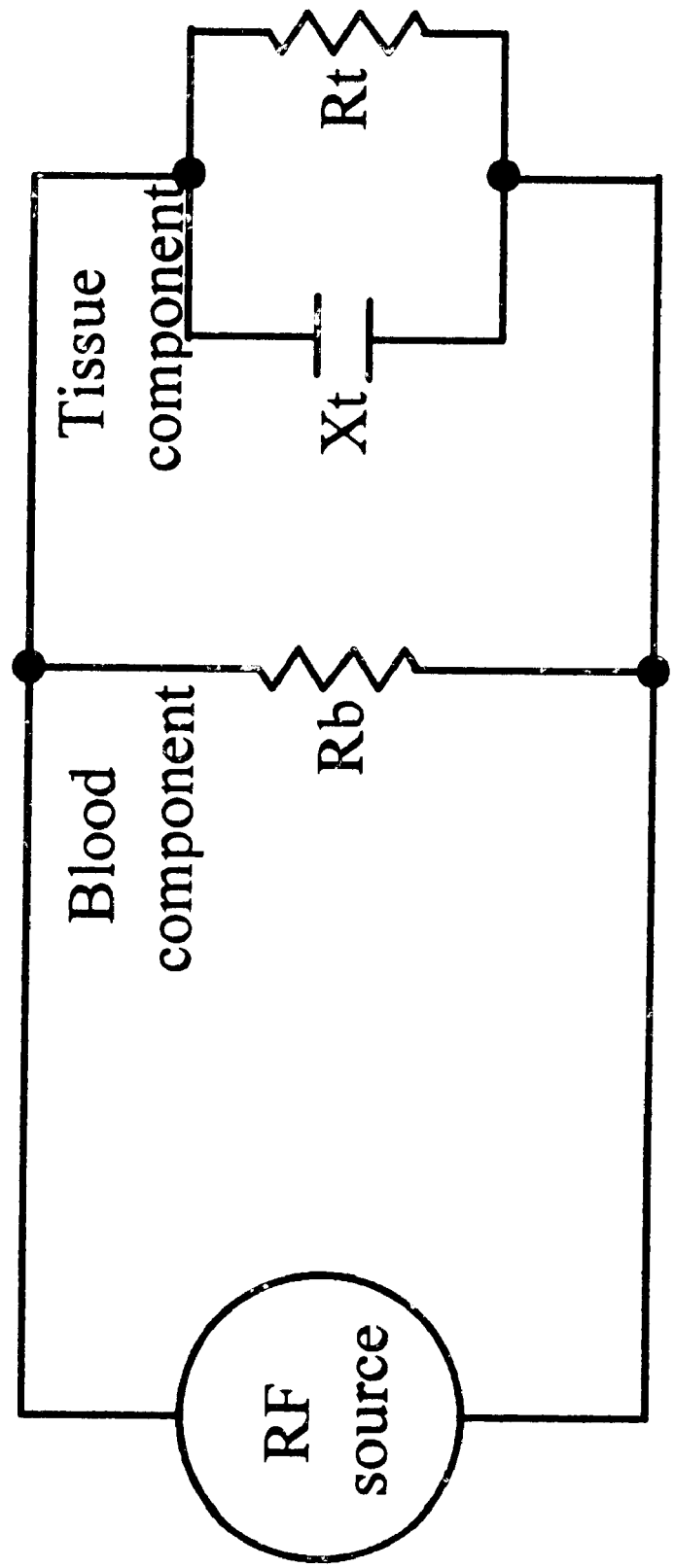
FIG. 1 is a schematic electrical circuit representing the blood and tissue current pathways according to the model of the invention.

This invention lies in the recognition that particular electrical parameters (impedance, frequency and phase angle) can be used to predict tissue temperature, assess lesion formation, and regulate the application of RF energy during cardiac tissue ablation procedures. We recognized that a conventional RF ablation system consists of a combination of components that constitute, and therefore can be advantageously modeled and analyzed as, an electrical circuit. In a tissue ablation system a current is produced either between two catheter electrodes placed in the heart (bipolar apparatus), or between a catheter electrode in the heart and an exterior plate electrode placed against the body of the patient (unipolar apparatus). Thus, in both types of apparatus the current flows between electrodes through parallel paths in the liquid blood phase and the solid tissue phase. Since blood is an electrolytic solution, its impedance is essentially resistive in nature. On the other hand, the cellular heart tissue includes membranes as well as liquids (so called lipid bilayers), which result in the tissue's impedance having both a resistive component and a capacitive-reactance component. This distinction between the electrical properties of blood and tissue and the discovery of useful correlations between bulk impedance and operating parameters of the ablation procedure provide the basis for this invention. Referring to the drawings, wherein like parts are designated throughout with like numerals and symbols, FIG. 1 represents a schematic electrical model of the blood/tissue components of an RF ablation system according to the invention. The blood path is characterized by a bulk resistance $R_b$, while the tissue path includes a bulk resistive component $R_t$ and a bulk capacitive-reactance component $X_t$, as mentioned above. Thus, the blood/tissue combination will have an overall impedance $Z = R - jX$ (this equation reflects the absence of inductive components), where R results from the contribution of both Rb and Rt, while X results from Xt. It is noted that bulk parameters are used because of the very complicated structure and composition of both the blood and tissue components, which would require a much more complicated model at the structural and chemical level. We found that the use of bulk parameters permits the use of the parallel current-flow model of FIG. 1 with good approximation to experimental results.

As would be obvious to one skilled in the art, the inverse of impedance, admittance, is defined by the quantity $$Y=1/Z=G-jB, \qquad (1)$$

where G is the system's conductance, related to its resistive component by the equation $G=R/(R^2+Xc^2)$, and B is its susceptance, related to the capacitive-reactance component by the equation $B=Xc/(R^2+Xc^2)$. (It is noted again that no meaningful inductive components are present in the tissue-blood system of the invention.) Accordingly, the conductance and susceptance of the system are equivalent measures of its resistance and reactance properties and can be used interchangeably to practice the invention.

Figure 2:
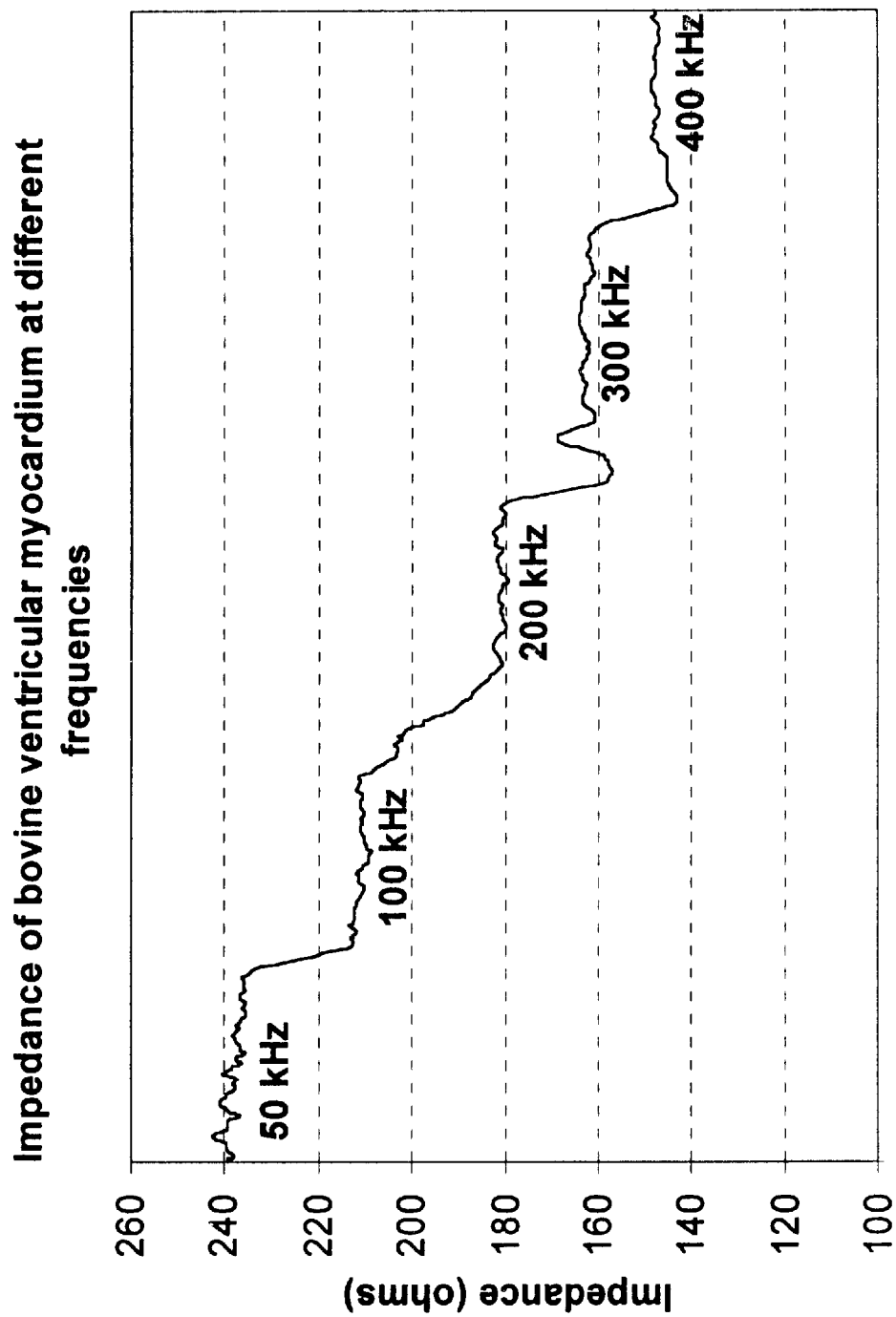
FIG. 2 is a plot of empirical data for bovine heart tissue showing a strong correlation between bulk impedance and the typical radio frequency applied during an ablation procedure.

The capacitive reactance Xc in an electrical circuit is related to frequency according to the equation $$Xc=1/(2\pi fC), \qquad (2)$$

where f is the frequency and C is the capacitance of the system. Accordingly, the capacitive reactance Xt of the tissue path, and correspondingly the bulk reactance and bulk impedance of the blood/tissue combination, can be expected to vary with the frequency of the current applied during the ablation procedure. This relationship was confirmed experimentally, as illustrated in the plot of FIG. 2.

Thus, according to one aspect of the invention, the frequency dependence of system impedance is used advantageously to determine the degree of contact between the ablation electrode and the heart tissue (that is, the ratio of tissue-to-blood interface area with the electrode). After the electrode is positioned as well as possible in the heart through fluoroscopic monitoring, the impedance of the system Z is calculated at two very different frequencies, for example 5 KHz and 1 MHz, on the basis of the voltage V and the corresponding current I through the system, which can be measured with standard instrumentation.

Using basic electrical theory, $$Z=V/I. \qquad (3)$$

If the impedance Z is found to remain substantially constant at the two frequencies, the system is taken not to include a capacitive component, which means that the current flow is substantially through blood and no tissue is being contacted by the electrode. In such case, the electrode is repositioned in the heart. If, on the other hand, the impedance is found to vary with frequency, the difference in impedance is used as a measure of the tissue-to-blood ratio of interface (contact) with the electrode. We found that using the change of impedance with respect to its value when the electrode is not in contact with tissue as a measure of the electrode/tissue interface, and assuming a linear relationship between impedance change and tissue-to-blood interface ratio, it is possible to assess the electrode/tissue interface very advantageously for improving the placement of the electrode prior to and during the ablation procedure. Based on impedance values Zb, Zw1 and Zw2, corresponding to measurements carried out in blood only (to provide a baseline value), at a low frequency w1 and a high frequency w2, respectively, the tissue-to-blood interface ratio can be usefully estimated by the relation $$\text{ratio}=K(Zw1-Zw2)/Zb, \qquad (4)$$

where K is an empirical proportionality constant accounting for electrode size and other system parameters. Alternatively, noting that the value of Zb tends to equal Zw2 at relatively high frequencies because Xc (measured by Xt) tends to zero (see Equation 2), the tissue-to-blood interface ratio can also be advantageously approximated by the similar relation $$\text{ratio}=K(Zw1-Zw2)/Zw2. \qquad (5)$$

In practice, since the heart being monitored is moving and may cause the position of the electrode to change, the two impedance measurements are preferably conducted contemporaneously by utilizing two separate RF sources and corresponding voltage and current meters, or equivalent apparatus. The overall current through the blood/tissue system is then appropriately filtered to separate the low and high frequency components required to calculate the respective impedances Zw1 and Zw2, as is well understood by those skilled in the art.

Since the estimate of the tissue-to-blood interface ratio is based on a change in the capacitive component of the system, it is noted that it could be carried out as well at a single frequency by measuring an electrical parameter indicative of such a change. For example, phase angle is such a parameter, as further detailed below. By measuring the phase angle between the current and voltage at the electrode, the capacitance of the system can be calculated by conventional electrical theory and the ratio can be estimated by $K\Delta C/C$, an expression similar to Equation 5, where K is an empirical proportionality constant, C is the capacitance when the electrode is in contact with tissue, and $\Delta C$ is a measured capacitance change observed during the procedure.

It is known that tissue temperature must exceed about 45–50° C. in order to be able to ablate tissue. It is also known that for any given electrode size and tissue contact area, RF-induced lesion formation and size, normally measured in terms of its volume, are a function of RF-power level and exposure time. However, the amount of heat generated decreases rapidly as the distance from the ablating electrode increases (resistive tissue heating decreases with the fourth power of such distance); and at higher power levels the exposure time is frequently limited by a marked rise in the electrical impedance at the electrode (which prevents the application of further heating energy). This has been shown to be preventable by regulating the electrode-tissue interface temperature to less than 100° C. Finally, we know that when excessive RF power is applied tissue heating is greatest at the surface interface with the electrode, where coagulation and/or tissue charring may occur and cause rapid impedance rise. Thus, the limiting factors for a catheter electrode in creating deeper lesions are the potential risk of coagulation on the electrode and tissue charring at the site that causes a rapid impedance rise.

According to another aspect of the present invention, these shortcomings can be avoided by monitoring and controlling tissue temperature as a function of changes in tissue resistance, and by estimating the depth of ablation as a function of changes in tissue reactive capacitance. As illustrated in FIG. 1, the tissue impedance, Zt, is due to a resistive component, Rt, and a reactance component, Xt. We discovered that changes in the tissue impedance during heating at the ablating frequency is due to a transient thermodynamic effect which is resistive and reversible (a change in Rt), and to a permanent effect due to cell damage that changes the tissue capacitance because of cell membrane destruction (a change in Xt). Moreover, Xt causes a phase shift between current and voltage in the RF ablation system (because of its capacitance component) measured by a phase angle θ determined by the well known general relation $$\theta = \arc \tan(X/R) \quad (6)$$

For the purposes of this invention, the term "phase angle" is defined as the angle that separates the voltage phase from the current phase (since the system includes mostly resistive and capacitive components, voltage lags current).

Figure 3:
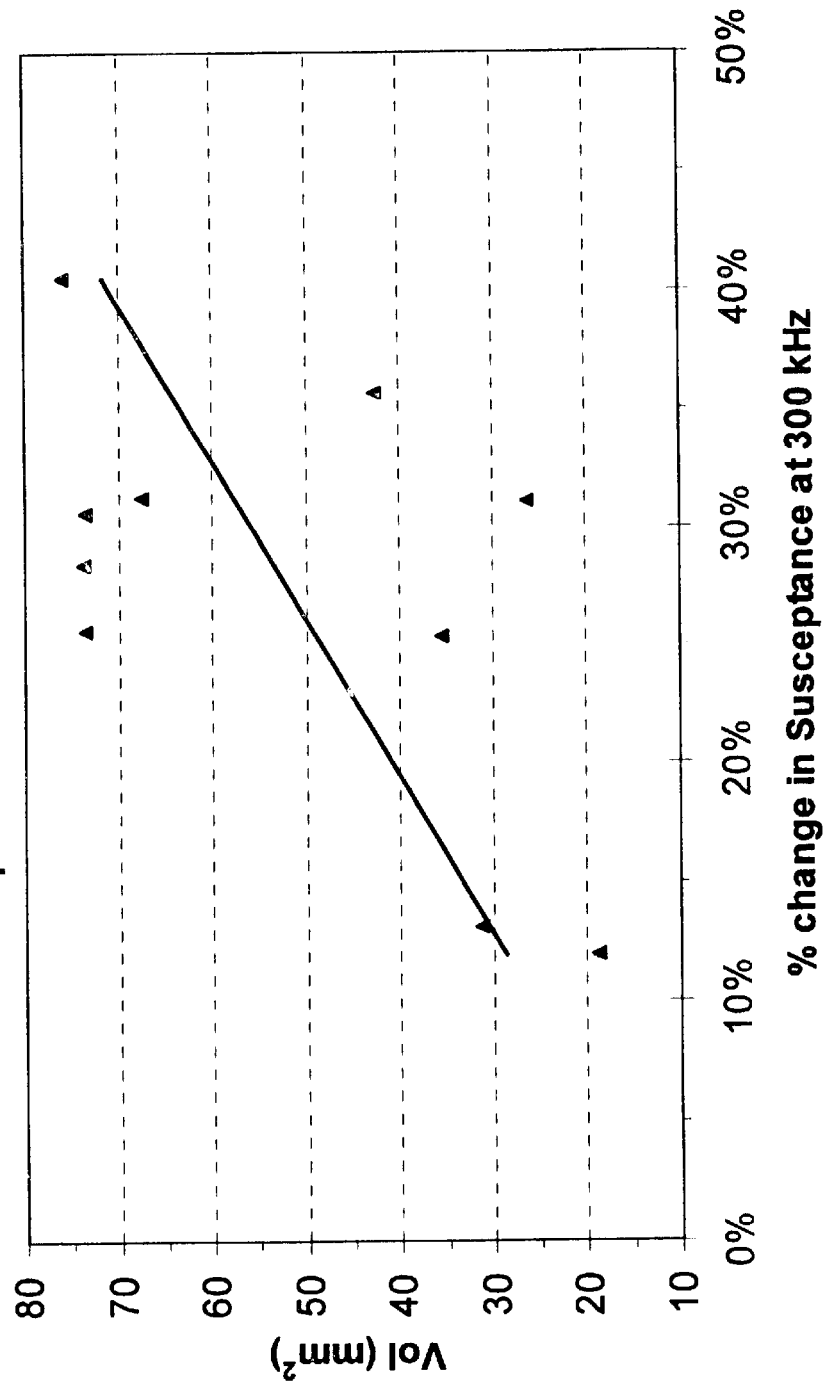
FIG. 3 is a plot of empirical data for bovine endocardium tissue showing a correlation between changes in bulk susceptance (resulting from changes in its capacitive component) and the degree of lesion formation in the tissue, as expected, during an ablation procedure.
Figure 4:
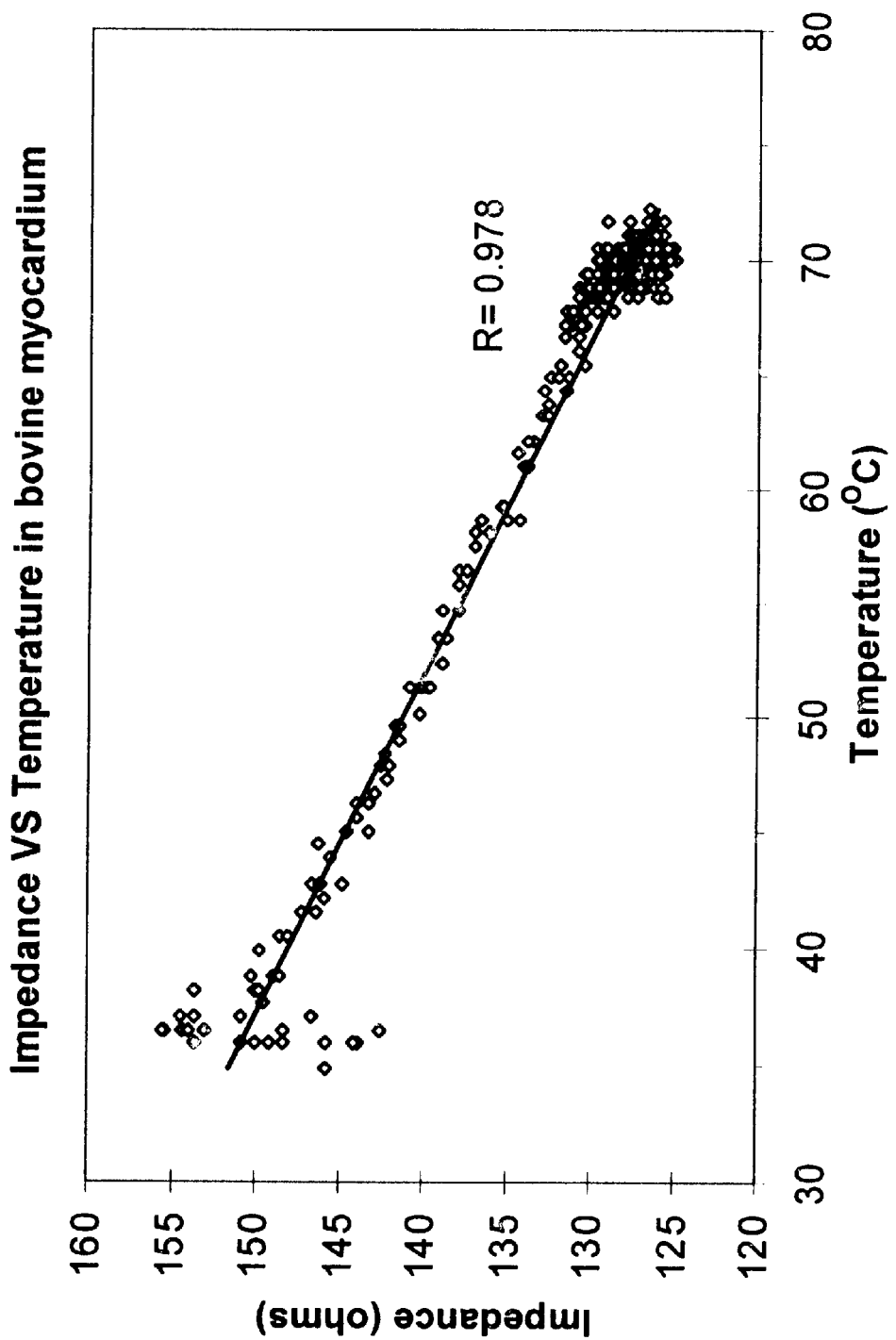
FIG. 4 is a plot of empirical data for bovine ventricular myocardium tissue showing a strong correlation between the resistive component of impedance (as measured by bulk impedance) and the tissue temperature, as recorded during an ablation procedure.
Figure 5:
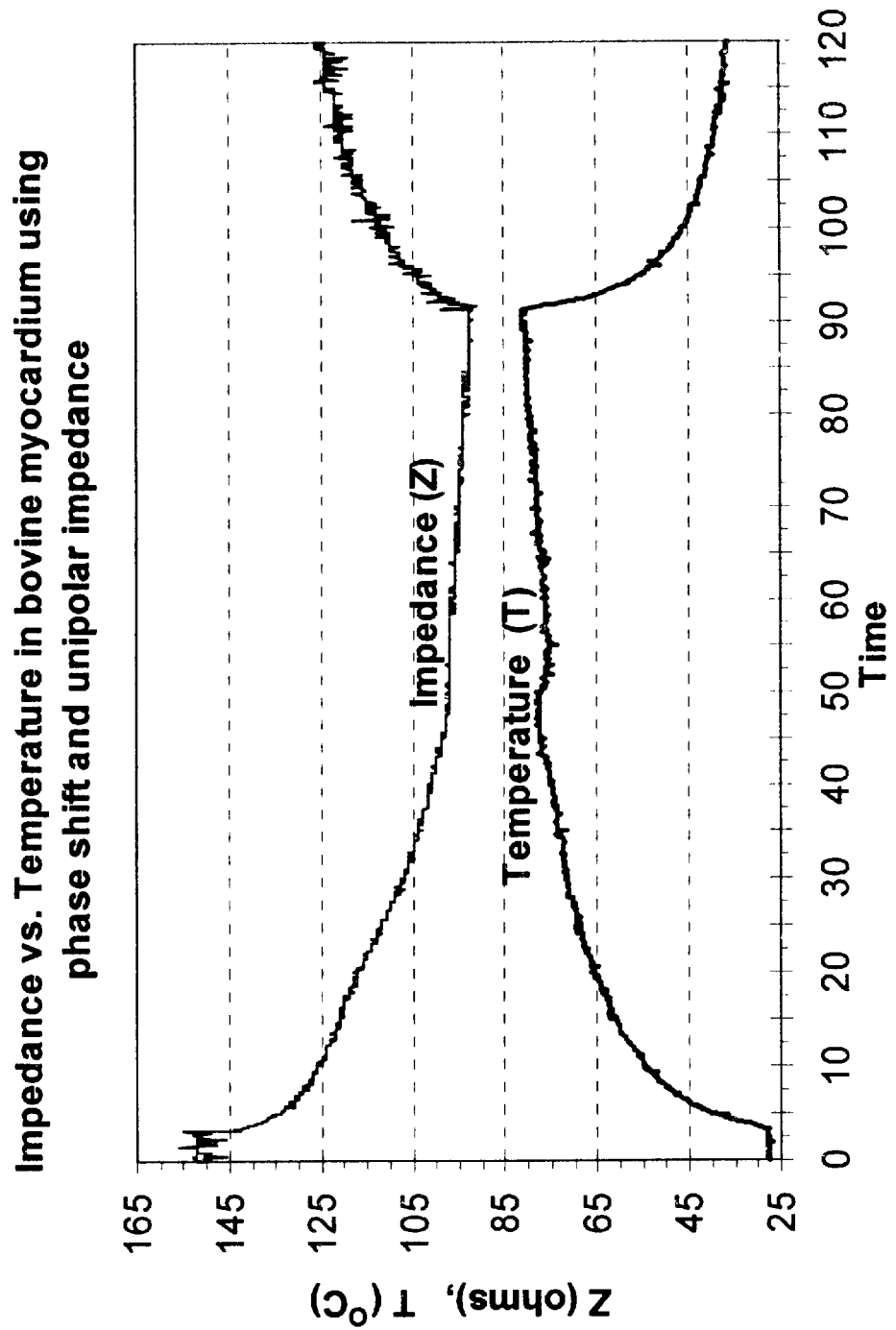
FIG. 5 is a plot of tissue bulk impedance and temperature versus time recorded during an ablation procedure of bovine ventricular myocardium tissue.

The changes in tissue structure produced by the formation of lesions affect its capacitance properties, thereby causing a change in Xt which in turn also induces a change in the phase angle separating current from voltage. This property can be used advantageously according to the invention to assess the condition of the lesion being produced by the ablation procedure. We found that by measuring electrical parameters related to the capacitive component of the system's impedance, either with θ measurements at a single frequency or Z measurements at different frequencies, it is possible to isolate the two components of Z (resistance R and reactance X) and therefore to monitor their changes. We found that ΔC (or, equivalently, ΔX or ΔB,, which can be calculated from θ measurements at a single frequency or from ΔZ measurements at distinct frequencies) has a significant correlation with lesion formation, as illustrated in the plot of FIG. 3. We also found that Z measurements correlate very well with tissue temperature, as shown in FIGS. 4 and 5, and in Table 1 below for measurements made at the electrode interface, at 2.5 mm and at 5.0 mm intra-tissue locations at various RF operating levels.

TABLE 1

| RF Voltage | Absolute Value of Correlation between Bulk Impedance and Temperature | | |
|---|---|---|---|
| | 0 mm | 2.5 mm | 5.0 mm |
| 34 | 0.98 | 0.95 | 0.88 |
| 44 | 0.93 | 0.93 | 0.96 |
| 53 | 0.90 | 0.90 | 0.88 |

These parameters can be calculated by measuring Z and frequency or phase angle during the ablation procedure. Thus, they can be used to regulate the applied power to keep the ablation process within acceptable bounds and to assess lesion formation.

Figure 6:
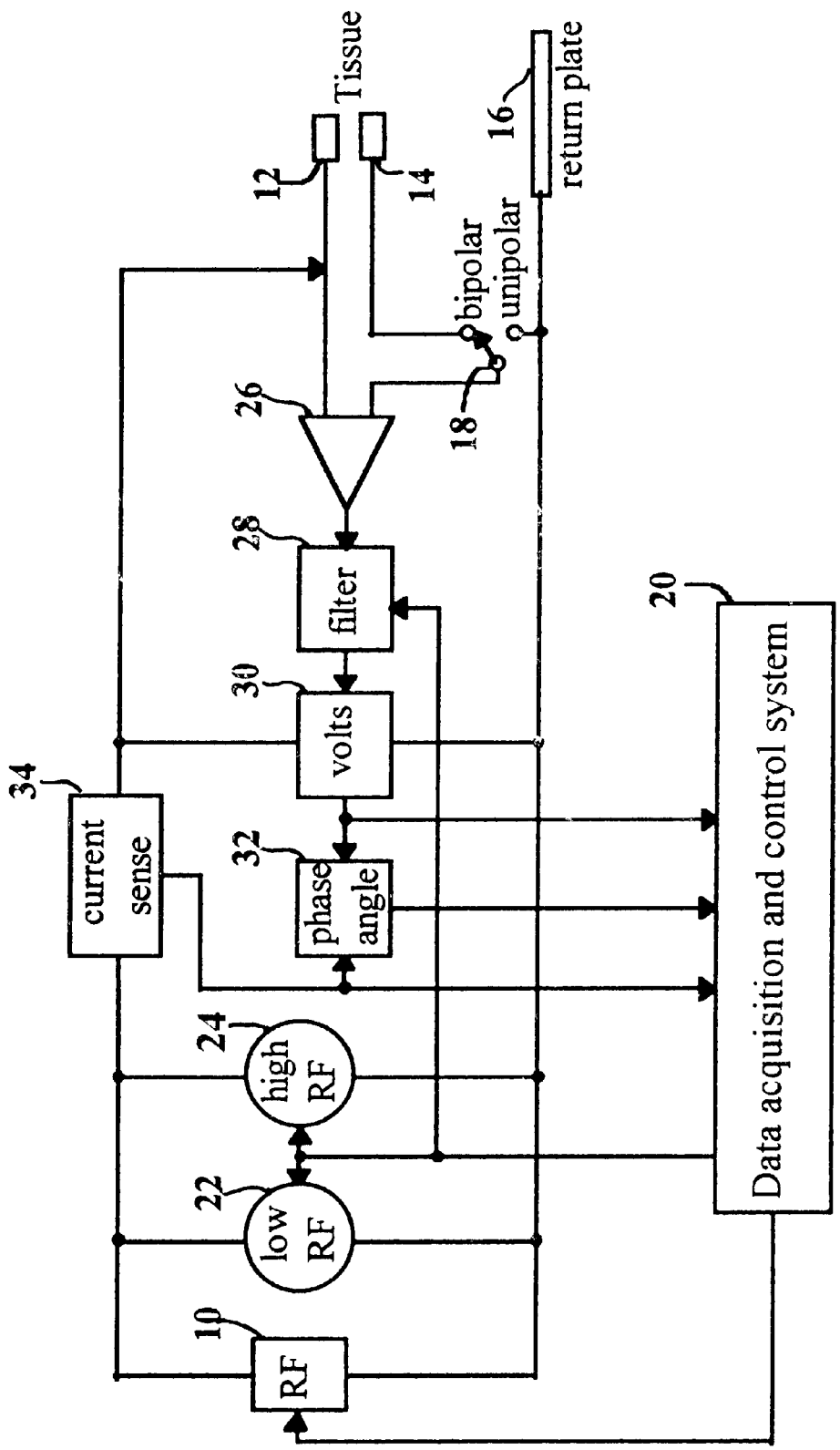
FIG. 6 shows schematically the system components required to carry out the invention.

In practice, the procedure is conducted using apparatus illustrated schematically in FIG. 6. A fixed level of RF power is delivered from an ablation power source 10 a catheter electrode 12 in contact with cardiac tissue T and the electrical circuit is completed either using another catheter electrode 14 in the heart or an exterior plate 16. A switch 18 is provided to permit operation under either mode. The RF source 10 is typically operated in the 250–500 KHz frequency range and in the 2–50 W power range. A desired current flow, typically in the 50–500 mA range, is maintained and the voltage is adjusted by a data acquisition and control module 20 to ensure a constant power input to the electrodes. Concurrently, low energy signals (less than 1 mW and less than 1 mA) are produced at relatively very low and very high frequencies (the preferred boundaries of the range are 5 KHz and 1 MHz) by RF power sources 22 and 24, respectively. Low- and high-frequency currents are similarly set and the corresponding voltages adjusted to produce constant power outputs at each frequency. The voltage signals passed through an amplifier 26 and a filter 28 are measured by a sensor 30 for each frequency. Similarly, the phase angle θ between voltage and current is measured by a sensor 32 at each frequency. The net current through the system may also be measured by a sensor 34.

Figure 7:
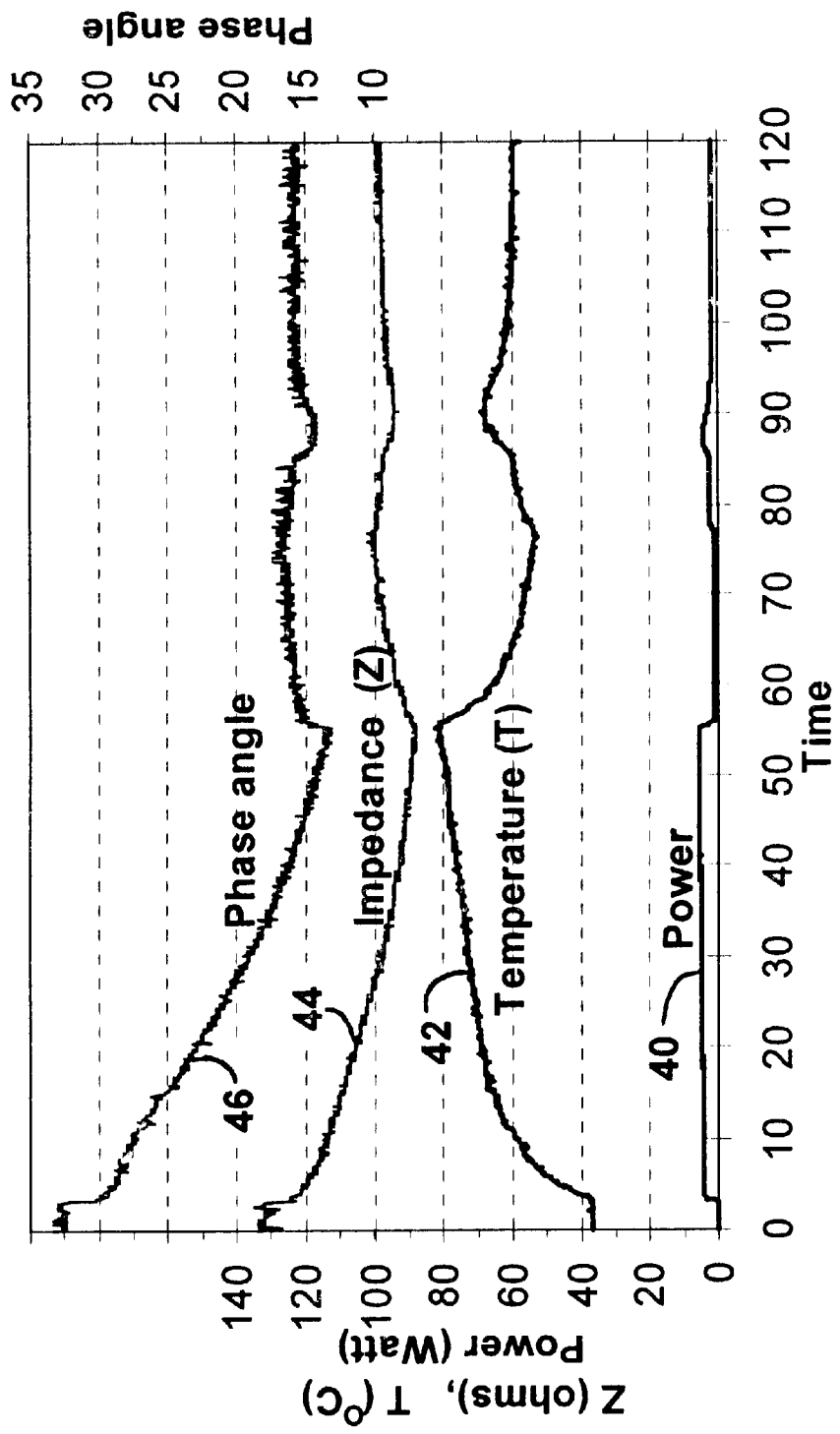
FIG. 7 is a graphical illustration of how phase angle, bulk impedance and tissue temperature vary in time with RF power delivery to the system during a typical ablation procedure, from which one embodiment of the invention can be practiced.

According to one embodiment of the invention, Z and θ are measured during the ablation procedure. As shown in the exemplary plot of FIG. 7, in response to the application of a constant power input by the source 10 illustrated by the step curve 40, the tissue temperature Tt (curve 42) is known to rise in substantial correlation with changes in tissue resistance Rt. At sufficiently low frequencies, the parallel impedance model of FIG. 1 becomes substantially resistive in nature, as would be expected by one skilled in the art. Accordingly, changes in tissue resistance Rt cause corresponding changes in its impedance Zt and, as expected, in the bulk impedance Z, which is also found to correlate well with tissue temperature (curve 44). Therefore, based on empirical correlation data, actual tissue temperature estimates can be made by tracking the bulk impedance of the ablation circuit. When the impedance reaches a predetermined value known to correspond to a maximum desirable temperature, the RF power source is turned off to avoid exceeding that temperature. In particular, the ablation procedure is preferably discontinued when tissue temperature reaches about 95° C.

Figure 8:
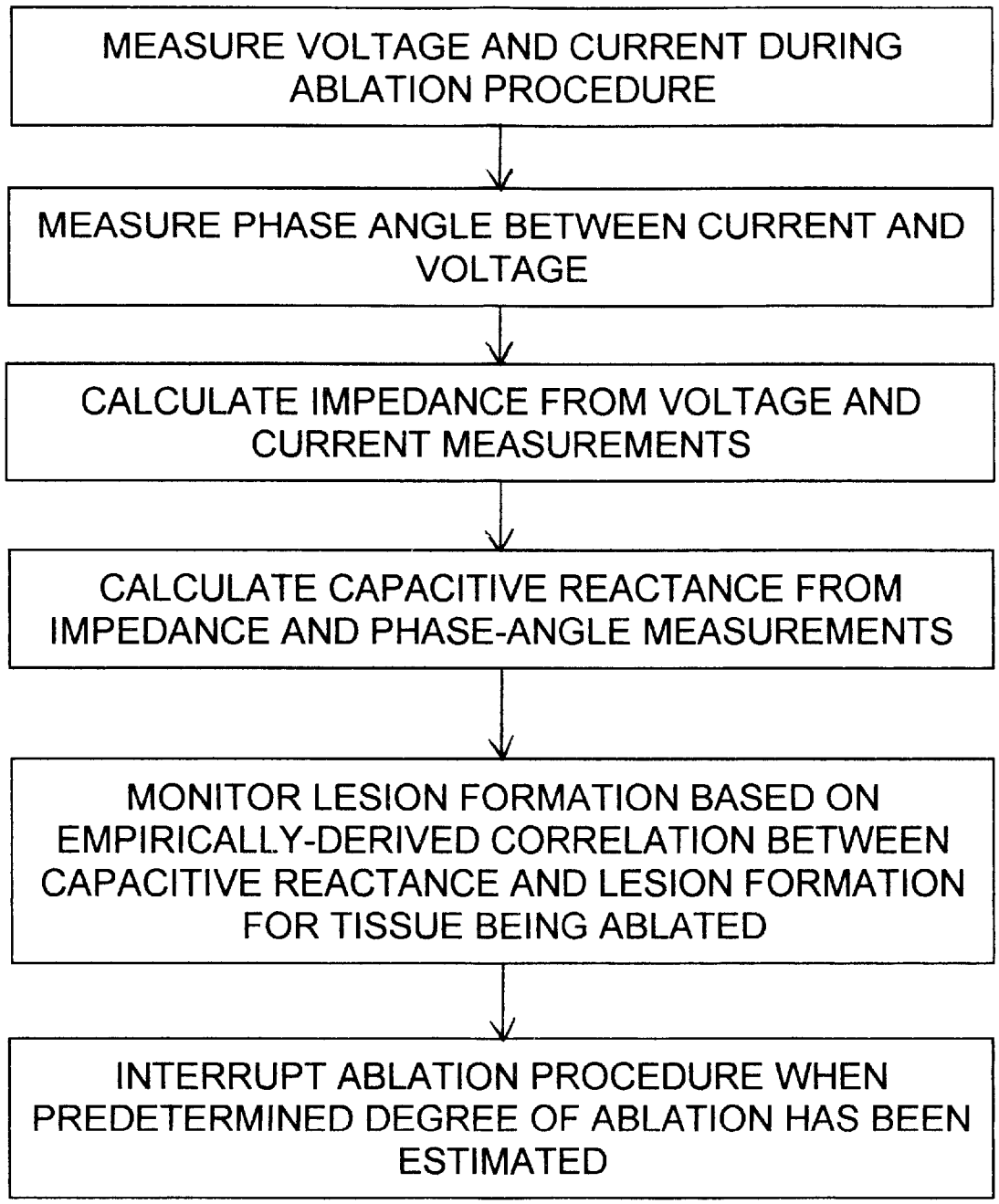
FIG. 8 is a block diagram of the steps of the method of the invention of FIG. 7 for estimating tissue temperature and lesion progress as a function of bulk impedance and phase-angle measurements.

Similarly, the phase angle θ can be tracked during the procedure (curve 46) as a measure of the degree of lesion produced by the electrode. At all times during ablation, a measured value of θ can be used to calculate R/X (Equation 6); also, from a corresponding measurement of Z and the relation Z=R−jX, both current values of X or C can be calculated. When C (or any equivalent parameter indicative of the capacitive component of the system, such as reactance or susceptance) reaches a desired value, the ablation procedure is terminated to avoid damaging the heart by excessive ablation. Empirical data relating quantitatively lesion and X for a given applied power are used to determine optimal termination points for various kinds of tissues. This procedure is outlined in FIG. 8.

Figure 9:
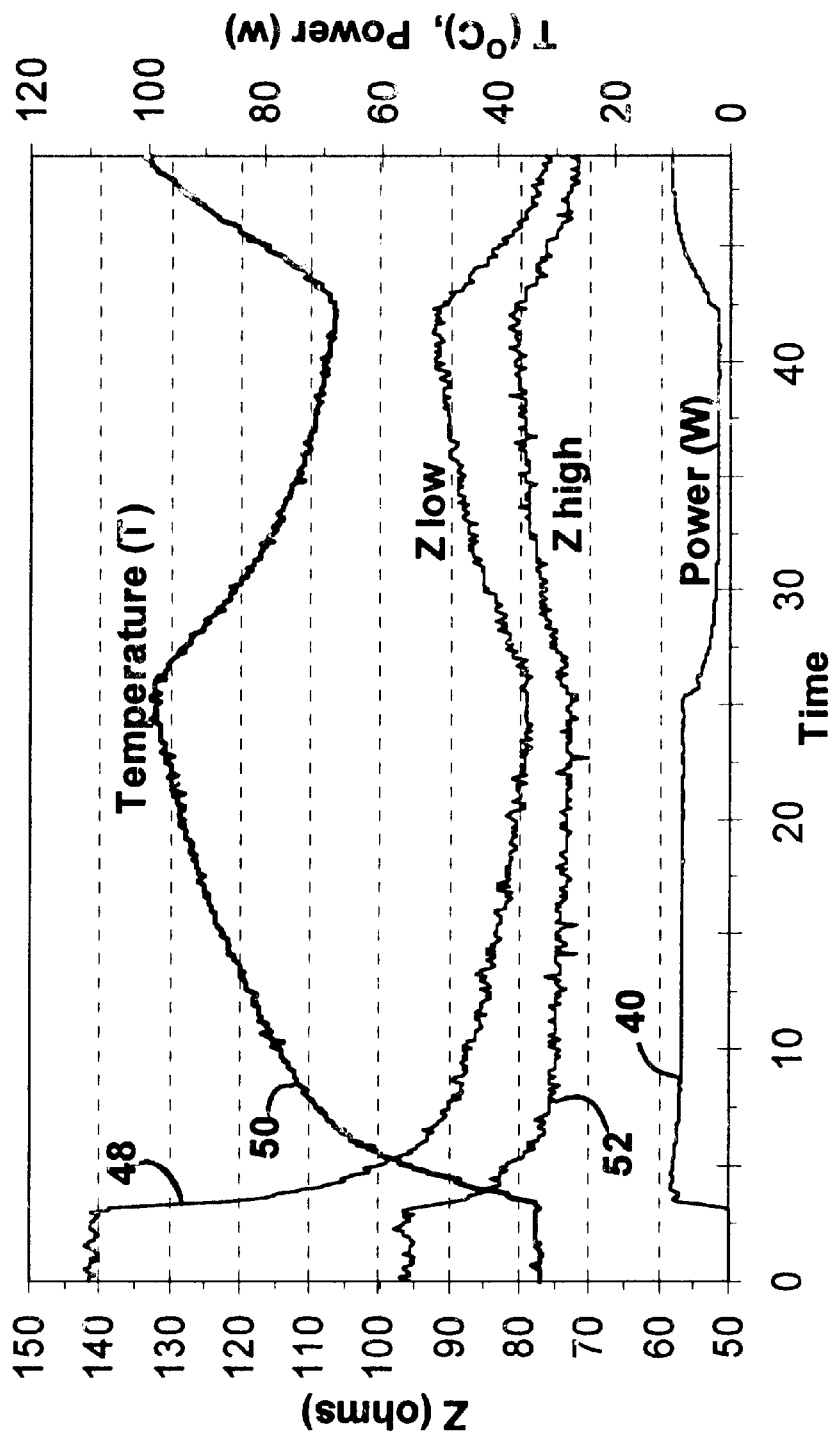
FIG. 9 is a graphical illustration of how bulk impedance parameters measured at a very low and a very high frequency vary with RF power delivery to the system during a typical ablation procedure, from which another embodiment of the invention can be practiced.

According to another embodiment of the invention, impedance measurements carried out at two distinct frequencies during the ablation procedure are used to track the tissue temperature and lesion progress. Rather than measuring impedance and phase angle at the frequency of the ablation RF source, though, Z measurements are made at relatively low and high frequencies ($Z_{low}$ and $Z_{high}$ such as and preferably at about 5 KHz and 1 MHz, respectively) using the RF power generators 22 and 24. Since the low-frequency impedance $Z_{low}$ of the circuit of FIG. 1 is known to be mainly resistive in nature, it is expected to track the resistive behavior of the system and is therefore used to monitor tissue temperature, as illustrated by curves 48 and 50 in FIG. 9. On the other hand, the difference between high- and low-frequency impedance is known to vary as a function of cell destruction because of its corresponding change in tissue capacitance. Therefore, $Z_{high}$ and $Z_{low}$ (curves 52 and 48, respectively) are tracked to measure the progress of tissue ablation and the procedure is terminated when a predetermined change has occurred. These impedance data can be used in various ways to calculate the change in tissue capacity, as would be clearly understood by one skilled in the art. One preferred way is to operate in the admittance domain, Y, where its conductance and susceptance components can be combined for the circuit of FIG. 1. Based on Equation 3, it is possible to calculate the change in capacitance of the tissue in straightforward manner from the two-frequency impedance measurements $Z_{low}$ and $Z_{high}$. Corresponding admittances are calculated from the expressions $Y_{low}=1/Z_{low}=G_{low}-jB_{low}$ and $Y_{high-1/Zhigh}=G_{high}-jB_{high}$. Since the low-frequency admittance $Y_{low}$ is known to have negligible contribution from the tissue's capacitance, it is taken to be equal to its resistive component; furthermore, since the resistive component is not affected by frequency, it is approximately constant over the frequency range. That is, $Y_{low}=G_{low}=G_{high}$. Accordingly, the capacitive component of the system, the effect of which is noticeable only at high frequencies, can be measured by the difference between the bulk admittances at the two test frequencies; that is, $B_{high}=Y_{high}-Y_{low}$. Thus, if desired, the capacitance of the circuit, C, can be calculated from $B_{high}$ using the well known relations $B=Xc/(R^2+Xc^2)$ and $X=1/(2\pi fC)$. Therefore, it is possible to track changes in the actual capacitance of the tissue as a function of bulk impedance variations and to use empirically derived tissue-capacitance/temperature correlations to practice the invention.

Figure 10:
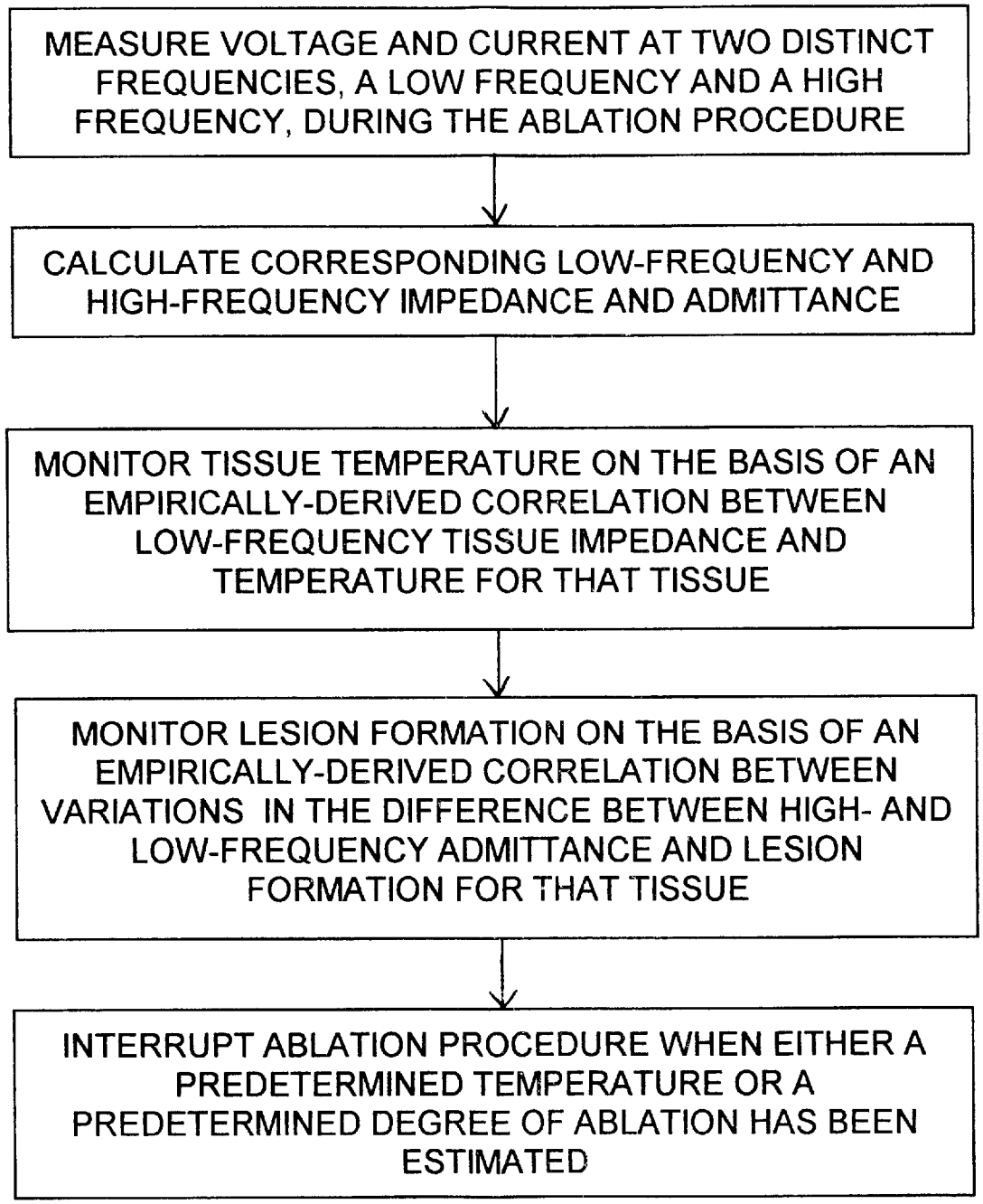
FIG. 10 is a block diagram of the steps of the method of the invention of FIG. 9 for estimating tissue temperature and lesion progress as a function of bulk impedance measurements at different frequencies.

In practice, the difference in admittance $(Y_{high}-Y_{low})$ reflects the change in susceptance for the system, $\Delta B$, which is directly related to a change in capacitance. Therefore, this information by itself can be used advantageously to estimate lesion progress. Again, empirical data relating lesion depth and $\Delta B$ (or equivalent parameters) at a given applied power are used to determine optimal termination points for various kinds of tissues. This procedure is outlined in FIG. 10.

Thus, it has been shown that useful correlations discovered to exist in the electrical circuit of an ablation system between tissue temperature and bulk impedance (used as an indirect measure of tissue impedance), and between tissue ablation and phase angle (or related capacitive parameters), can be used advantageously to monitor progress during the procedure. The temperature rise of the tissue can be monitored, so that a physician can receive current feedback information about the onset of the ablation process at the interface with the tissue and about potential impending tissue carbonization and/or blood coagulation due to excessive temperature rise. The degree of ablation can similarly be followed, so that the physician can terminate the procedure when a desired depth of lesion is reached. These parameters are not measured directly, but experiments have shown a very high correlation to exist between them and the electrical parameters used for carrying out the invention. Thus, the disclosed methodology can be applied to any ablation process simply by developing the pertinent correlation data necessary for estimating temperature and lesion progress for a given tissue. In addition, the invention provides a reliable quantitative measure of the tissue-to-blood ratio of interface with the electrode, so that electrode positioning can be optimized at the start of the ablation procedure.

It is important to note that the heart of the invention is the realization that the impedance characteristics of the ablation system and the capacitive nature of tissue can be exploited through the measurement of appropriate electrical parameters to estimate tissue temperature and lesion formation during the ablation procedure. The invention has been described in terms of ablation produced by an RF energy source, but it could be practiced as well with other sources, such as ultrasound and cryogenic, so long as electrical parameters related to the resistive and capacitive components of the tissue can be measured and correlated to tissue temperature and lesion formation.

It is understood that any number of functional equivalents may exist in lieu of the preferred embodiments described above. Accordingly, changes in the details, parameters, steps and apparatus that have been described may be made by those skilled in the art within the principles and scope of the invention illustrated herein and defined in the appended claims. For example, power sources using different frequency ranges could be used either alone or in combination with additional ablation devices to monitor and control the ablation procedure according to methodology equivalent to the invention. Therefore, while the present invention has been shown and described in what is believed to be the most practical and preferred embodiment, it is recognized that departures can be made therefrom within the scope of the invention, which is therefore not to be limited to the details disclosed herein but is to be accorded the full scope of the claims so as to embrace any and all equivalent products and methods.

We claim:

1. A method of monitoring tissue lesion formation during a tissue-ablation surgical procedure, comprising the following steps:

administering electrical power at predetermined voltages and corresponding currents to a tissue in contact with an ablation device;

measuring an electrical parameter related to a capacitive component of the tissue; and tracking said tissue lesion formation on the basis of a known correlation between said electrical parameter and tissue lesion formation for said tissue;

wherein said tissue is cardiac tissue.

2. The method of claim 1, wherein said electrical parameter is a phase angle between said voltages and corresponding currents, and said known correlation is between a capacitive parameter related to phase angle and tissue lesion formation for said tissue.

3. The method of claim 1, wherein said electrical parameter is a capacitive component of tissue impedance, and said known correlation is between changes of said capacitive component and tissue lesion formation for said tissue.

4. The method of claim 3, wherein said capacitive component is calculated from said voltages and corresponding currents measured during the procedure.

5. The method of claim 1, wherein said ablation device is an electrode and said surgical procedure is carried out with radio-frequency electrical energy.

6. The method of claim 1, further comprising the step of terminating said surgical procedure when said tissue lesion formation is estimated to reach a predetermined amount.

7. In a tissue-ablation surgical procedure wherein an ablating energy is administered to a tissue in contact with an ablation device immersed in a liquid, a method of estimating a ratio of tissue-to-liquid interface area with the device comprising the following steps:

(a) administering electrical power at predetermined voltages and corresponding currents to the tissue in contact with said ablation device;

(b) measuring an electrical parameter related to a capacitive component of the tissue;

(c) calculating said capacitive component of the tissue; and (d) estimating said ratio on the basis of a change in said capacitive component.

8. The method of claim 7, wherein said electrical parameter is phase angle.

9. The method of claim 7, wherein said electrical parameter is impedance and steps (c)–(d) are accomplished by the following steps:

measuring said voltages and corresponding currents at a first frequency of operation and calculating corresponding first values of tissue admittance;

measuring said voltages and corresponding currents at a second frequency of operation and calculating corresponding second values of tissue admittance; and estimating said ratio on the basis of a difference between said first and second values of tissue admittance.

10. The method of claim 7, wherein said tissue is cardiac tissue.

11. The method of claim 7, wherein said liquid is blood.

12. The method of claim 7, wherein said ablating energy is radio-frequency electrical energy and said ablation device is an electrode.

13. In a tissue-ablation surgical procedure wherein an ablating energy is administered to a tissue in contact with an ablation device, a method for concurrently monitoring tissue temperature and tissue-lesion formation during the surgical procedure, comprising the following steps:

(a) administering ablating electrical power to the tissue in contact with said ablation device at a predetermined ablating frequency;

(b) concurrently with step (a), administering a low-frequency electrical power to the tissue in contact with said ablation device at a predetermined low-frequency voltage and a corresponding low-frequency current, wherein said low-frequency electrical power is administered at a low frequency below said ablating frequency;

(c) concurrently with steps (a) and (b), administering a high-frequency electrical power to the tissue in contact with said ablation device at a predetermined high-frequency voltage and a corresponding high-frequency current, wherein said high-frequency electrical power is administered at a high frequency above said ablating frequency;

(d) measuring said low-frequency voltage and corresponding low-frequency current and said high-frequency voltage and corresponding high-frequency current;

(e) calculating a low-frequency impedance, a low-frequency admittance, and a high-frequency admittance based on data collected in step (d);

(f) tracking said tissue temperature on the basis of a known correlation between temperature and said low-frequency impedance in the tissue; and (g) tracking said tissue-lesion formation on the basis of a known correlation between lesion formation in said tissue and a difference between said high-frequency admittance and low-frequency admittance in the tissue.

14. The method of claim 13, wherein said tissue is cardiac tissue.

15. The method of claim 13, wherein said ablating energy is radio-frequency electrical energy and said ablation device is an electrode.

16. The method of claim 13, wherein said ablating frequency is about 250–500 kHz, said low frequency is about 5 KHz, and said high frequency is about 1 MHz.

17. The method of claim 13, further comprising the step of terminating said surgical procedure when the tissue temperature is estimated to reach about 95° C.

18. The method of claim 13, further comprising the step of terminating said surgical procedure when said tissue-lesion formation is estimated to reach a predetermined amount.

19. A radio-frequency electrical apparatus for performing an ablation operation on a tissue, comprising:

an electrode adapted for placement against said tissue;

an ablation radio-frequency generator capable of energizing said electrode at a predetermined ablation frequency to produce ablation of the tissue;

a low-frequency generator capable of administering a low-frequency electrical power to the tissue in contact with said electrode at a predetermined low-frequency voltage and a corresponding low-frequency current, said low-frequency electrical power being administered at a low frequency below said ablating frequency;

a high-frequency generator capable of administering a high-frequency electrical power to the tissue in contact with said electrode at a predetermined high-frequency voltage and a corresponding high-frequency current, said high-frequency electrical power being administered at a high frequency above said ablating frequency;

means for measuring said low-frequency voltage and corresponding low-frequency current and said high-frequency voltage and corresponding high-frequency current;

means for calculating a low-frequency impedance, a low-frequency admittance, and a high-frequency admittance based on data collected by said measuring means;

means for tracking a temperature of said tissue on the basis of a known correlation between tissue temperature and said low-frequency impedance; and means for tracking a tissue-lesion formation on the basis of a known correlation between lesion formation in said tissue and a difference between said high-frequency admittance and low-frequency admittance.

20. The radio-frequency electrical apparatus of claim 19, wherein said tissue is cardiac tissue, said ablating frequency is about 250–500 kHz, said low frequency is about 5 KHz, and said high frequency is about 1 MHz.

21. The radio-frequency electrical apparatus of claim 19 further comprising means for terminating said ablating operation when said tissue-lesion formation is estimated to reach a predetermined amount.

22. The radio-frequency electrical apparatus of claim 21, wherein said means for terminating said ablating operation includes means for controlling an output of said ablation radio-frequency generator in response to a signal related to at least one of said low-frequency impedance and said difference between the high-frequency admittance and the low-frequency admittance.

* * * * *